United States Patent [19]

Dejaifve et al.

[11] Patent Number: 4,975,407
[45] Date of Patent: Dec. 4, 1990

[54] CATALYST FOR DEHYDROGENATING ORGANIC COMPOUNDS, A PROCESS FOR ITS PREPARATION AND ITS USE

[75] Inventors: Pierre E. Dejaifve, Amsterdam, Netherlands; Roland A. C. Garin, Grande Couronne; Jean-Claude Lambert, Grande Couronne; Jean-Paul Darnanville, Grande Couronne; Jean-Claude Clement, Grande Couronne, all of France

[73] Assignee: Shell Oil Company, Houston, Tex.

[21] Appl. No.: 343,228

[22] Filed: Apr. 26, 1989

[30] Foreign Application Priority Data

Apr. 29, 1988 [FR] France ................................ 88 05764

[51] Int. Cl.$^5$ ............................................. B01J 23/78
[52] U.S. Cl. ..................................... 502/330; 502/338; 502/344; 423/593; 423/594
[58] Field of Search ..................... 502/330, 338, 344; 423/593, 594

[56] References Cited

U.S. PATENT DOCUMENTS

| | | | |
|---|---|---|---|
| 3,644,549 | 2/1972 | Innes et al. | 585/442 |
| 3,810,973 | 5/1974 | Arendt et al. | 423/594 |
| 3,862,910 | 1/1975 | Cichowski | 502/213 |
| 3,862,997 | 1/1975 | Walker | 502/213 |
| 3,929,979 | 12/1975 | Bamberger et al. | 423/594 |
| 3,998,757 | 12/1976 | Foster | 502/314 |
| 4,220,560 | 9/1980 | Anquetil et al. | 502/307 |
| 4,480,051 | 10/1984 | Wu | 502/338 |
| 4,658,074 | 4/1987 | Bajars et al. | 585/493 |
| 4,675,170 | 6/1987 | Hibst et al. | 423/594 |
| 4,684,619 | 8/1987 | Moore | 502/330 |

Primary Examiner—Anthony McFarlane

[57] ABSTRACT

Dehydrogenation catalyst, wherein the molar ratio between iron oxide providing agent and potassium oxide providing agent calculated as iron: potassium atomic ratio is in the range of from 1.5 to 60, a $K_2Fe_{1\text{-}2}O_{19}$ phase is present in an octahedral $Fe_3O_4$ matrix, showing crystalline epitaxy between the hexagonal structure of $K_2Fe_{12}O_{19}$ and the (111) planes of the $Fe_3O_4$ spinel structure, and showing intense X-ray diffraction peaks in the area of from $d=12.4$ Å to $d=1.60$ Å.

Process for the preparation of such catalyst and process for dehydrogenation of optionally substituted alkanes into olefins.

23 Claims, No Drawings

CATALYST FOR DEHYDROGENATING ORGANIC COMPOUNDS, A PROCESS FOR ITS PREPARATION AND ITS USE

FIELD OF THE INVENTION

The invention relates to a catalyst for dehydrogenating organic compounds, a process for its preparation and its use. The catalyst is preferred for dehydrogenation of ethylbenzene to styrene.

BACKGROUND OF THE INVENTION

More particularly the invention relates to a catalyst for dehydrogenating organic compounds such as optionally substituted alkanes or aralkyls, which is at least derived from iron oxides and potassium oxide. Such catalysts are in principle known from e.g. U.S. Pat. Nos. 3,644,549, 3,998,757 and 4,220,560, British Pat. Nos. 1,152,484, 1,550,873 and 2,091,757B.

However, all these patents disclose the use of catalyst compositions for dehydrogenation of alkanes, optionally substituted by an aryl and more particularly a phenyl group, which are containing in addition to iron and potassium one or more other metals included in a spinel or perovskite structure, in order to enhance the activity and/or the selectivity of this dehydrogenation of more particularly ethyl benzene.

Due to the present economic requirements, research for further improved catalyst systems, showing an improved activity and selectivity and obtainable by using more simple metal ingredient mixtures, has continued.

An object of the present invention is therefore to provide such improved catalyst systems, which may be manufactured in an economically attractive way by using rather simple starting compositions and which may meet the present economical requirements as to dehydrogenation processes.

SUMMARY OF THE INVENTION

The instant invention relates to a catalyst derived from iron oxides providing agents and potassium oxide providing agents, characterized in that the molar ratio between iron oxide providing agent and potassium oxide providing agent calculated as iron: potassium atomic ratio is in the range of from 1.5 to 60 and that a potassium ferrite $K_2Fe_{12}O_{19}$ phase is present supported on an octahedral $Fe_3O_4$ matrix, showing crystalline epitaxy between the hexagonal structure of $K_2Fe_{12}O_{19}$ and the (111) planes of the $Fe_3O_4$ spinel structure. Preferably crystalline particles sizes are in the range of from 0.5–15 lm and more preferably the crystalline particle size varies in the range of from 1–10 pm. The catalysts are suited for the dehydrogenation of organic compounds, particularly to the dehydrogenation of ethylbenzene to styrene in the presence of steam.

DETAILED DESCRIPTION OF THE INVENTION

The catalyst compositions according to the present invention will show the most intense X-ray diffraction peaks in the area of from $d=12.4$ Å to $d=1.60$ Å (Ångström = $10^{-10}$). The preferred catalytic compositions will show X-ray diffraction peaks at d-spacings $d=11.9$ Å, 2.83 Å and 2.65 Å providing strong indication to the occurrence of the $K_2Fe_{12}O_{19}$ phase.

It will be appreciated that the most attractive properties of the present catalysts were found if an additional phase consisting of $KFe(III)O_2$ does not occur at all or only in minor amounts in the final composition.

It has been found that in order to reach the most attractive catalytic activities, the thickness of the involved hexagonal $K_2Fe_{12}O_{19}$ plates will vary in the range of from 40 to 240 Ångstroms. This thickness of the hexagonal $K_2Fe_{12}O_{19}$ plates has been measured by AUGER spectroscopy.

An important advantage of these catalysts of the present invention, containing tailored $Fe_3O_4$ octahedra, is the extreme stability shown by a zero deactivation rate at relative low temperatures and a 6.7 steam/hydrocarbon molar ratio as compared to well known prior art catalysts, which all deactivate significantly under such low steam conditions applied for e.g. the conversion of ethylbenzene into styrene.

Moreover the formation of by-products with such conversion has been found to be significantly lowered, leading to a selectivity improvement of 1.5–2.0 point, as determined at 70% conversion of ethylbenzene.

The catalytic compositions according to the present invention may be obtained by a process, which forms another feature of the present invention.

This process comprises reacting a ferroso-ferric oxide providing agent, optionally mixed with a potassium oxide providing agent, at a temperature in the range of from 300°–1000° C., at a pressure in the range of from 100 to 1000 bar and in the presence of a solvent under supercritical conditions, acting as a reducing agent, and rapid quenching of the reaction mixture, followed by mixing or impregnating the obtained octahedral ferroso-ferric oxide with a potassium oxide providing agent and calcination of the mixture at a temperature in the range of from 300°–1000° C. under an inert atmosphere.

By the term "inert atmosphere" is meant an atmosphere not interfering with the desired conversion of ferroso-ferric oxide and the potassium providing agent, e.g. nitrogen and rare gases.

By the terms "ferroso ferric oxide providing agent" and "potassium oxide providing agent", as used throughout the specification, are meant a great variety of suitable iron and potassium compounds, providing the particularly desired oxides under the before-mentioned reaction conditions.

As suitable ferroso ferric oxide providing agent may be used e.g. iron oxide, iron hydroxide, goethite (α-FeOOH), iron carbonate, iron oxalate, iron nitrate, iron nitrite, iron chloride, iron bromide, iron fluoride, iron chlorate, iron bromate, iron acetate, iron sulphide, iron citrate, iron tartrate, iron lactate, iron thiosulfate, iron sulfite, the valence of iron being preferably three.

The potassium oxide providing agent which optionally may be present in the starting ferroso-ferric oxide providing agent may be selected from potassium carbonate, potassium hydrogenocarbonate, potassium nitrate, potassium oxalate, potassium nitrite, potassium fluoride, potassium chloride, potassium bromide, potassium iodide, potassium pyrosulphate, potassium peroxydisulphate, potassium chlorate, potassium bromate or potassium iodate.

Preferably as suitable solvent a lower alcohol is used, containing from 1 to 4 carbon atoms and more preferably 2 or 3 carbon atoms.

Most preferred conditions have found to be obtained by mixing the alcohol with water in an amount of from 20 to 100% by volume of the alcohol content.

More preferably as ferroso-ferric oxide providing agent are used: goethite (α-FeOOH), hydrated iron oxide Fe(OH)$_3$nH$_2$O, iron acetate, iron nitrate, iron nitrite, iron citrate or mixtures thereof The calcination of the ferroso-ferric oxide with a potassium oxide providing agent will usually take place over a period of from 25 0.5 to 10 hours and more preferably from 4–8 hours.

It was found that the potassium oxide providing agent which is added by mixing or impregnation to a previously formed ferroso-ferric oxide phase, must provide a non-reducing atmosphere when converted into potassium oxide under the calcination conditions, in order to avoid the formation of significant proportions of a potassium rich ferrite phase (KFe(III)O$_2$) and to reach most attractive catalytic activities.

Therefore suitable potassium oxide providing agents are selected in this stage from potassium nitrate, potassium nitrite, potassium pyrosulphate, potassium peroxydisulphate, potassium iodate, potassium chlorate, potassium bromate and the like, or mixtures thereof.

More preferably potassium nitrate or potassium nitrite or mixtures thereof are used.

In order to obtain the desired hereinbefore described catalytic properties an amount of 1 to 25% by weight, preferably of 5 to 20% by weight of potassium oxide have to be added, calculated as the total weight of potassium oxide and iron oxides.

More preferably amounts of potassium in the range of from 10 to 15% by weight are used.

It will be appreciated that these total potassium amounts may be partially introduced during the "high pressure" process for the manufacture of the ferroso-ferric oxide phase and the remainder will be included in this preformed phase by mixing or impregnation with an aqueous solution of the applied potassium compound.

The process steps for the manufacture of the catalytic compositions of the present invention preferably carried out at temperatures in the range of from 350° to 850° C., whereas the ferroso-ferric oxide phase forming step is preferably carried out at pressures in the range of from 350 to 750 bar.

The processing time for the ferroso-ferric oxide phase forming step will normally vary in the range of from 6 to 12 hours and more preferably of from 8 to 10 hours.

The processing time for the ferroso-ferric oxide phase —K$_2$Fe$_{12}$O$_{19}$ phase forming step will normally take from 1–4 hours.

It will be appreciated that after incorporation of the potassium oxide providing agent involved in the ferroso-ferric oxide phase, by impregnation with an aqueous solution or dry mixing of the components followed by addition of sufficient water to obtain a paste, the mixture may be extruded to the particles of the desired form before the calcination step. For example particles may be formed in the shape of pellets, tables, spheres, pills, saddles, trilobes or tetralobes, starting from a paste, wherein preferably also a polyalcohol is included, such as sorbitol, mannitol, glycerol and the like as stabilizing auxiliary. However, the mixtures of the ferroso-ferric oxide phase and the potassium oxide providing agent may also be coated on a suitable carrier. The obtained extruded particles or the coated carrier may subsequently be calcined to form the desired final catalytic composition.

Moveover, it was found that the temperature time profile during the last stage of the preparation of the catalytic composition is very important for the catalytic properties of the final composition.

More particularly it was found that relatively short quenching times caused predominantly relatively large ferroso-ferric oxide octahedra crystallites (1 μm and larger), while a slow cooling of the calcined catalyst composition caused predominantly significantly smaller crystallites (0.1–0.3 μm), mixed with large crystallites.

It will be appreciated that another feature of the invention is formed by the use of the catalytic compositions of the present invention for the dehydrogenation of optionally substituted alkanes into the corresponding olefins, and more particularly for the dehydrogenation of ethylbenzene into styrene. More preferably the catalytic compositions are used in a process using low steam conditions in order to enable manufacture of olefins at decreased costs.

However, the dehydrogenation can also successfully be applied to other organic compounds and more particularly compounds which contain from 2 to 20 carbon atoms and at least one

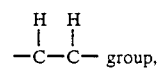

have a boiling point below about 350° C. Such compound may contain other elements, in addition to carbon and hydrogen, such as oxygen, halogens, nitrogen and sulphur. Preferred are compounds having from 2 to 12 carbon atoms and especially preferred compound containing 2 to 10 carbon atoms.

Among the types of organic compounds which are successfully dehydrogenated to the corresponding unsaturated derivative by means of the process of the present invention are nitriles, amines, alkyl halides, ethers, esters, aldehydes, ketones, alcohols, acids, alkyl aromatic compounds, alkyl heterocyclic compounds, cycloalkanes, alkanes and alkenes.

Illustrative dehydrogenations may convert propionitrile to acrylonitrile, propionaldehyde to acrolein, ethyl chloride to vinyl chloride, methyl isobutylate to methyl methacrylate, 2,2 dichlorobutane to chloroprene, ethyl pyridine to vinyl pyridine, ethylbenzene to styrene, isopropylbenzene to α-methyl styrene, ethylcyclohexane to styrene, cyclohexane to benzene, ethane to ethylene, propane to propylene, isobutane to isobutylene, n-butane to butene and 1.3-butadiene, butene to 1.3 butadiene, n-butane to vinyl acetylene, methyl butene to isoprene, cyclopentane to cyclopentene and 1.3 cyclopentadiene, n-octane to ethyl benzene and ortho-xylene, monomethylheptanes to xylenes ethyl acetate to vinylacetate and 2,4,4-trimethylpentane to xylenes.

The temperature for the dehydrogenation reaction is generally at least about 250° C. and the maximum temperature in the reactor may be about 750° C. More particularly the process may be carried out at temperatures in the range of from 450° C. to 650° C.

The dehydrogenation reaction may be carried out at atmospheric pressure, superatmospheric pressure or at sub-atmospheric pressure.

The total pressure of the system will normally be about or in excess of atmospheric pressure, although subatmospheric pressure may also desirably be used.

Generally, the total pressure will be less than about 5 bar (75 p.s.i.a) and excellent results can be obtained at about atmospheric pressure.

It will be appreciated that the organic compound can be dehydrogenated in the absence of steam or by treatment with steam optionally mixed with predetermined amounts of oxygen or air, i.e. either non-oxidative or oxidative embodiments of the dehydrogenation process may be applied.

Preferably the dehydrogenation process is carried out using a molar ratio of steam to alkane and more particularly alkylbenzene in the range of from 2 to 20 and more preferably in the range of from 5 to 13.

The dehydrogenation processes are suitably carried out using a liquid hourly space velocity in the range of from 0.1 to 5.0 liter of alkylbenzene per liter catalyst per h, using for example a tubular or radial flow reactor or a quick contact downflow reactor containing a circulating solid.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The invention will be described by the following examples which are provided for illustration purposes and are not to be construed as limiting the invention.

EXAMPLE 1

A sample of 98 g of crystalline ferroso-ferric oxide, $Fe_3O_4$-spinel structure, showing by electron microscopy octahedral crystallites having an average particle size of 10 μm was obtained as follows. 275 g of predried $Fe(OH)_3 \cdot 6H_2O$ were mixed with 450 ml of a 50-50 (by volume) ethanol-water solution and poured in an autoclave. The temperature was progressively increased till 240° C., maintained at 240° C. for 2 hours, increased to 415° C. in a 4 hours period and finally maintained at this temperature for 2 hours. During the first two hours of the process, the internal pressure increased to 690 bars, and was kept constant at this value till the end of the process. After a rapid quenching, a solid powder was recovered, dried overnight at 110° C. (under nitrogen) and characterized by X-ray diffraction (pure $Fe_3O_4$) and electronic microscopy (octahedral morphology, average crystallite particle sizes: 10 μm).

A dehydrogenation catalyst containing "87.6% by weight, $Fe_3O_4$, 12.4% by weight $K_2O$" was prepared by impregnation technique, using 56 g of the above-described $Fe_3O_4$ powder and an aqueous solution of potassium nitrate (impregnation volume: 0.5 ml per g of powder). After drying overnight at 120° C., the catalyst was calcined under nitrogen at 800° C. for 2 hours. X-ray diffraction spectrum shows clearly the formation of a hexagonal potassium ferrite phase, $K_2Fe_{12}O_{19}$; moreover, electronic microscopy techniques demonstrate the epitaxial growth of the hexagonal potassium ferrite on the (111) crystal planes of the $Fe_3O_4$ spinel structure.

A mixture of ethylbenzene and steam heated to a certain temperature, was introduced into a reactor and led over 10 ml of catalyst, prepared as described above, pelletized, crushed and sieved into 0.25-0.42 mm solid particles.

The mixture was conducted at atmospheric pressure and a liquid hourly space velocity of one liter ethylbenzene per liter catalyst and per hour through the catalyst bed.

The temperature was adjusted so that the conversion of ethylbenzene was 70%. The reaction product leaving the reactor was analyzed by means of gas-liquid chromatography. From the data obtained, the temperature at 70% conversion and the selectivity to styrene was calculated.

The steam to ethylbenzene molar ratio was first adjusted to 12, the temperature of the catalyst was adjusted until the conversion of ethylbenzene was 70% ($T_{70}$). The selectivity to styrene at 70% conversion is indicated as $S_{70}$.

It is well known in the art that lowering the catalyst temperature and the steam to ethylbenzene ratio induces catalyst deactivation. Thus, the stability of the catalyst was determined at low temperature ($\leq 575°$ C.) and using a molar ratio steam to ethylbenzene $\leq 7.0$ by determining the average increase of the temperature which was necessary to keep the conversion of ethylbenzene at the constant value in each experiment. This average increase of temperature is indicated as "°C./day".

In the table, the $T_{70}$-$S_{70}$ and °C./day values are given. It can be seen that $S_{70}$ is 94.5% at $T_{70}=615°$ C., and activity losses are zero at steam to ethylbenzene ratio of 6.7 and 1.3° C./day at a lower 5.4 steam to ethylbenzene ratio. Such a catalyst appears thus to be highly selective (>94%) and extremely stable at steam to ethylbenzene molar ratio as low as 6.7.

EXAMPLE 2

The same recipe as in Example 1 was repeated, using 182 g of iron hydroxide.

A solid powder (65 g) was recovered, dried overnight at 110° C. under nitrogen, consisting of crystalline $Fe_3O_4$ (X-ray diffraction) with pure octahedral morphology (electron microscopy-, average crystallite particle size: 5 μm).

A dehydrogenation catalyst containing 87.6% by weight $Fe_3O_4$ and 12.4% by weight $K_2O$, was prepared as described in Example 1, using 64.35 g of the $Fe_3O_4$ powder and an aqueous solution of potassium nitrate (impregnation volume: 0.5 ml per g of powder). After the calcination step, the epitaxial growth of $K_2Fe_{12}O_{19}$ on the (111) crystal planes of $Fe_3O_4$ octahedra was again observed (X-ray diffraction and electronic microscopy).

The catalyst activity, selectivity and stability were determined in the same experimental conditions as in Example 1. As shown in the Table, the catalyst of Example 2 is also highly selective (94.2%) and extremely stable at a steam to ethylbenzene molar ratio as low as 6.8.

COMPARATIVE EXAMPLE A

This example, not according to the invention, shows that impregnation of $Fe_3O_4$ octahedra with an aqueous potassium carbonate solution could lead to poorer catalytic performance.

Octahedral crystallites of the $Fe_3O_4$ spinel (42 g, average crystallite particle size 1.3 μm) were obtained by the same process as described in the previous examples, using iron hydroxide $Fe[OH]_3$, $H_2O$ and isopropyl alcohol; the autoclave temperature was 405° C. for 6 hours, and internal pressure 450 bars.

The $Fe_3O_4$ powder was then impregnated with an aqueous solution of potassium carbonate, dried and calcined under nitrogen at 800° C. for 2 hours. Due to the CO/$CO_2$ atmosphere during the calcination step, a different, stable, potassium-rich ferrite is formed ($KFeO_2$-X-ray determination), instead of the hexagonal, easily reducible $K_2Fe_{12}O_{19}$ potassium-ferrite. Electron microscopy shows, besides $KFeO_2$ particles, crystalline pure $Fe_3O_4$ octahedra, partly eroded by the action of alkali.

As shown in the table, such a catalyst, containing $Fe_3O_4$ and $KFeO_2$ appears to be inactive in ethylbenzene dehydrogenation.

COMPARATIVE EXAMPLE B

This example, which is not representing an embodiment according to the invention, shows that the octahedral morphology of the $Fe_3O_4$ crystallites is essential to lead to highly selective and stable catalysts.

Spheric particles of $Fe_3O_4$ were obtained using the high temperature-high pressure technique described in examples 1 and 2, except that red —$Fe_2O_3$ was treated by pure ethanol in an autoclave.

A dehydrogenation catalyst "87.6% by weight $Fe_3O_4$, 12.4% by weight $K_2O$" was obtained, using the potassium nitrate impregnation technique described in examples 1 and 2. After calcination, the solid consists of the hexagonal potassium ferrite $K_2Fe_{12}O_{19}$, $Fe_3O_4$ and minor amounts of $KFeO_2$ and $K_2CO_3$ (from atm. $CO_2$ adsorption on free-$K_2O$).

This catalyst develops a lower selectivity (92.6%) than the catalysts prepared according to the invention.

COMPARATIVE EXAMPLES C AND D

These examples, which are not representing embodiments according to the invention, show the lower performance of catalysts prepared according to the more conventional method: the intimate mixing of solid articular $Fe_2O_3$ iron oxide with suitable promoters compounds, addition of water to obtain a paste, extrusion, drying and calcination.

Catalyst of comparative Example C, having the same K/Fe ratio as in examples 1 and 2, shows only 92.5% selectivity and deactivates significantly when operated under a steam: ethylbenzene ratio of 8.5 (2.3° C./day).

Catalyst of comparative Example D—(a sample of commercial Shell S.105 catalyst) leads only to 91.7% selectivity. Moreover, even with the presence of the chromium oxide stabilizer in its composition, it losses activity, when submitted to a steam to ethylbenzene ratio of 6.5 (0.9° C./day).

A comparison between Examples 1 and 2 and Examples B, C and D shows clearly the advantages on selectivity and stability catalytic performance of materials prepared and developing crystalline properties according to the invention (epitaxial growth of hexagonal $K_2Fe_{12}O_{19}$ on (111) crystalline planes of small, octahedral crystallites of $Fe_3O_4$).

TABLE

| Example No. | Catalyst "88$Fe_2O_3$.12$K_2O$" (wt) | | Potassium salt used | Catalyst X-RD phases* | S/EB = 12:1 (molar) EB (LHSV) = 1 h$^{-1}$ | | Stability: activity Loss (°C./day) | | | tested over |
|---|---|---|---|---|---|---|---|---|---|---|
| | Iron ox. starting material | | | | T(70)° C. | S(70)% | T° C. | S/EB | °C./day | |
| | Chem. Comp. | Morphology | | | | | | | | |
| 1 | $Fe_3O_4$ | octahedra | $KNO_3$ | $\underline{K_2Fe_{12}O_{19}}$ | 615 | $\underline{94.5}$ | 560 | $\underline{6.7}$ | $\underline{0.0}$ | 8 days |
| | | | | $Fe_2O_3$; $Fe_3O_4$ | | | 575 | 5.4 | 1.3 | 8 days |
| 2 | $Fe_3O_4$ | octahedra | $KNO_3$ | $\underline{K_2Fe_{12}O_{19}}$ | 613 | $\underline{94.2}$ | 560 | $\underline{6.8}$ | $\underline{0.0}$ | 7 days |
| | | | | $Fe_2O_3$; $Fe_3O_4$ ($KFeO_2$) | | | 575 | 5.4 | 1.2 | 7 days |
| Comp. A | $Fe_3O_4$ | octahedra | $K_2CO_3$ | $\underline{KFeO_2}$ $Fe_3O_4$ | >>630 | n.d. | — | | — | |
| Comp. B | $Fe_3O_4$ | spheric | $KNO_3$ | $\underline{K_2Fe_{12}O_{19}}$ $Fe_2O_3$; $Fe_3O_4$ ($KFeO_2$)($K_2CO_3$) | 606 | $\underline{92.6}$ | — | | — | |
| Comp. C | $Fe_2O_3$ | acicular | $K_2CO_3$ | $\underline{Fe_2O_3}$ $K_2CO_3$ ($K_2Fe_{12}O_{19}$) | 597 | $\underline{92.5}$ | 575 | $\underline{8.5}$ | $\underline{2.3}$ | 5 days |
| Comp. D | $Fe_2O_3$ | acicular | $K_2CO_3$ | Commercial Shell 105 | 596 | $\underline{91.7}$ | 560 | $\underline{6.5}$ | $\underline{0.9}$** | 5 days |

*main cryst. phase
**commercial S 105 contains chromium oxide, as a stabilizer, particularly when used under severe experimental conditions (low S/EB ratios). Other formulations are chromium-free.
( ) = traces/minor cryst. phase

We claim:

1. A dehydrogenation catalyst comprising iron and potassium oxides, derived from iron oxides providing agents and potassium oxide providing agents, characterized in that the molar ratio between iron oxide providing agent and potassium oxide providing agent calculated as iron: potassium atomic ratio is in the range of from 1.5 to 60 and wherein hexagonal plates of a $K_2Fe_{12}O_{19}$ potassium ferrite phase are epitaxially supported on (111) planes of octahedral crystallites of an $Fe_3O_4$ spinel matrix.

2. The dehydrogenation catalyst according to claim 1, characterized in having a crystalline particle size in the range of from 0.5–15 μm.

3. The dehydrogenation catalyst according to claim 2, characterized in that the crystalline particle size varies in the range of from 1 to 10 μm.

4. The dehydrogenation catalyst according to any one of claims 1, 2, or 3 characterized by having its most intense X-ray diffraction peaks in the area of from d=12.4 Å to d=1.60 Å.

5. The dehydrogenation catalyst according to claim 4, characterized by having its most intensive X-ray diffraction peaks at d=11.9 Å, 2.83 Å and 2.65 Å.

6. The dehydrogenation catalyst according to any one of the claims 1-3, characterized by hexagonal $K_2Fe_{12}O_{19}$ plates having a thickness in the range of from 40 to 240 Å.

7. The dehydrogenation catalyst according to claim 1, characterized in that is is substantially free from K Fe(III)O$_2$ phase.

8. A process for the preparation of a dehydrogenation catalyst, comprising reacting a ferroso-ferric oxide providing agent with itself at a temperature in the range of from 300°-1000° C., at a pressure in the range of from 100-1000 bar and in the presence of a solvent under superciritical conditions, acting as a reducing agent, and rapid quenching of the reaction mixture, to form a phase of octahedral crystallites of ferroso-ferric oxide, followed by mixing or impregnating the obtained ferroso-ferric oxide with a potassium oxide providing agent, and calcination of the mixture at a temperature in the range of from 300°-1000° C. under an inert atmosphere.

9. The process according to claim 37, characterized in that the ferroso-ferric oxide providing agent is selected from iron oxide, iron hydroxide, goethite(a-FeOOH), iron carbonate, iron oxalate, iron nitrate, iron nitrite, iron chloride, iron bromide, iron fluoride, iron chlorate, iron bromate, iron acetate, iron sulphide, iron citrate, iron tartrate, iron lactate, iron thiosulfate and iron sulphite.

10. The process according to claim 9, characterized in that the valence of iron is three.

11. The process according to claim 8, characterized in that a potassium oxide providing agent is mixed with the ferro-ferric oxide providing agent prior to reacting.

12. The process according to any one of claims 8, 9, 10 or 11, characterized in that the potassium oxide providing agent is selected from potassium carbonate, potassium hydrogenocarbonate, potassium nitrate, potassium oxalate, potassium nitrite, potassium fluoride, potassium chloride, potassium bromide, potassium iodide, potassium pyrosulphate, potassium peroxydisulphate, potassium chlorate, potassium bromate or potassium iodate.

13. The process according to claim 9 characterized in that the ferroso-ferric oxide providing agent is selected from goethite, hydrated iron oxide, iron acetate, iron nitrate, iron nitrite, iron citrate and mixtures thereof.

14. The process according to claim 12, characterized in that the potassium oxide providing agent is selected from potassium nitrate, potassium nitrate, potassium-pyrosulphate, potassium peroxydisulphate, potassium iodate, potassium chlorate, potassium bromate and mixtures thereof.

15. The process according to claim 12, characterized in that the potassium oxide providing agent is selected from potassium nitrate, potassium nitrite and mixtures thereof.

16. The process according to claim 14, characterized in that the potassium oxide providing agent is selected from potassium nitrate, potassium nitrite and mixtures thereof.

17. The process according to any one of the claim 8 characterized in that as solvent an alcohol containing from 1 to 4 carbon atoms is used.

18. The process according to claim 17, characterized in that the alcohol is mixed with water in an amount of from 20 to 100% by volume of the alcohol content.

19. The process according to any one of the claim 8 characterized in that temperatures in the range of from 350 to 850° C. are applied during the ferroso-ferric oxide phase forming steps and during the subsequent calcination.

20. The process according to any one of the claim 8 characterized in that pressures in the range of from 350 to 750 bar are applied during the ferroso-ferric oxide phase forming steps.

21. The process according to any one of the claim 8 characterized in that the processing time for the ferroso-ferric oxide phase forming step is in the range of from 6 to 12 hours.

22. The process according to claim 21, characterized in that the processing time is in the range of from 8 to 12 hours.

23. The process according to any one of the claim 8 characterized in that the calcination time is in the range of from 1 to 4 hours.

* * * * *